United States Patent [19]

Charlesworth et al.

[11] 4,266,185
[45] May 5, 1981

[54] PROBES AND APPARATUS FOR AND METHODS OF MEASURING CRACK DEPTHS

[75] Inventors: Frank D. W. Charlesworth, South Harrow; William D. Dover, Gerrards Cross; Kenneth A. Taylor, Knebworth, all of England

[73] Assignee: Dover & Partners Limited, London, England

[21] Appl. No.: 12,796

[22] Filed: Feb. 16, 1979

[51] Int. Cl.³ .......................................... G01R 27/14
[52] U.S. Cl. .................................. 324/64; 324/65 R
[58] Field of Search ..................... 324/64, 65 P, 65 R

[56] References Cited

U.S. PATENT DOCUMENTS

| | | | |
|---|---|---|---|
| 2,532,929 | 12/1950 | McBrayer | 324/65 R |
| 2,611,006 | 9/1952 | Delmhorst | 324/65 R |
| 3,267,418 | 8/1966 | Wolfe | 324/65 R |
| 3,303,418 | 2/1967 | Rose | 324/64 |
| 3,412,325 | 11/1968 | Soderling | 324/65 R |
| 3,504,664 | 4/1970 | Haddad | 324/65 R |
| 3,864,627 | 2/1975 | Shigo | 324/65 P |
| 3,876,935 | 4/1975 | Guillermie | 324/65 R |
| 3,916,304 | 10/1975 | Roemer et al. | 324/64 |
| 3,927,370 | 12/1975 | De Bough | 324/65 R |
| 4,048,558 | 9/1977 | Goodman | 324/65 R |

*Primary Examiner*—Stanley T. Krawczewicz
*Attorney, Agent, or Firm*—Kenyon & Kenyon

[57] ABSTRACT

The invention relates to probe for use in measuring crack depth in a conducting workpiece, apparatus including the probe for measuring crack depth and methods of measuring crack depth. The probe has a pair of spaced parallel electrodes mounted on a body and electrically insulated from each other. The probe includes a lead for each electrode. The leads extend in a twisted pair through the body and between electrodes to a point lying in or adjacent the plane containing the contact surfaces of electrodes. The leads then separate and extend directly to a respective one of electrodes and are connected thereto adjacent the contact surfaces thereof. The probe is used to detect crack depths by measuring and comparing potential difference between contact surfaces when the electrodes are engaged on cracked and uncracked portions of an electrically conducting workpiece, when an alternating current is passed through the workpiece.

17 Claims, 7 Drawing Figures

PROBES AND APPARATUS FOR AND METHODS OF MEASURING CRACK DEPTHS

This invention relates to electrical probes, apparatus and methods for measuring surface crack depths in electrically conducting workpieces.

The invention provides an electrical probe comprising a body, a pair of electrodes being mounted on the body at spaced locations thereon and projecting from the body, each electrode having a contact surface, the electrodes being electrically insulated from one another and a lead for each electrode, each lead having an input end and an output end, the input end of the lead being connected to a respective electrode, the leads and electrodes together constituting a non-inductive circuit.

The invention further provides an electrical probe comprising a body, a pair of electrodes for engaging a workpiece, the electrodes being mounted on the body at spaced locations thereon and projecting from the body, each electrode having a contact surface spaced from the body, the electrodes being electrically insulated one from the other, a lead for each electrode, the leads being arranged such that the area of the loop formed, in use, by the leads, the electrodes and the surface of the workpiece is negligible.

The invention still further provides an electrical probe comprising a body, a pair of electrodes for engaging a workpiece the electrodes being mounted on the body at spaced locations thereon and projecting from the body, each electrode having a contact surface spaced from the body, the electrodes being electrically insulated one from the other and a lead for each electrode, each lead having an input end and an output end, the two leads extending from respective output ends as a twisted pair, a shielded twisted pair or a coaxial cable to a position in or immediately adjacent a plane containing said contact surfaces of the electrodes, the leads separating at said position and extending directly to their respective electrodes, the input end of each lead being connected to its respective electrode adjacent the contact surface thereof.

Each electrode is constituted by an elongate member projecting longitudinally from the body, in which case each contact surface may be formed at the free end of its respective electrode.

According to another aspect of the invention there is provided an electrical probe comprising a body, a pair of electrodes for engaging the workpiece, the electrodes being mounted on the body at spaced locations thereon and projecting from the body, each electrode having a contact surface spaced from the body, the electrodes being electrically insulated one from the other, a lead for each electrode, each lead having an input and an output end, the two leads extending from respective output ends as a twisted pair between the electrodes and then separating and extending individually to their respective electrodes, the input end of each lead being connected to its respective electrode adjacent the contact surface thereof, and means for urging those portions of the lead, which extend between the twisted pair and the respective electrode, against the surface of a workpiece when, in use, the electrodes are positioned to engage the surface of the workpiece.

Preferably each electrode is constituted by an elongate member projecting longitudinally from the body, in which case each contact surface may be formed at the free end of its respective electrode.

The portions of the leads may be mounted or formed on one side of a flexible diaphragm and the means for urging may comprise means for exerting a pressure on the one side of the diaphragm. For example the means for exerting pressure may include a source of pressurized gas.

According to a still further aspect of the invention there is provided apparatus for measuring the depth of surface cracks in an electrically conducting workpiece comprising a pair of current input leads engageable on the workpiece on respective sides of the crack, means for passing an alternating current through the leads and through the workpiece, a probe as claimed in any one of the preceding claims and means for detecting a potential difference between the electrodes for the probe.

The means for detecting the potential difference between the electrodes may include a phase sensitive detector.

The invention still further provides a method for measuring the depth of the surface crack in an electrically conducting workpiece comprising the steps of passing an alternating current through that part of the workpiece which contains the crack, engaging a pair of spaced electrodes on the surface of the workpiece adjacent and on one side of the crack, measuring a potential difference between the electrodes, engaging the electrodes on the surface such that the crack runs between the electrodes whilst maintaining the separation of the electrodes, measuring the potential difference between the electrodes and calculating the crack depth in accordance with the formula $$E = (B/A - 1) \times D/2$$

wherein

E = the crack depth

A = the potential difference between the electrodes when the electrodes are engaged on the workpiece on the first mentioned position.

B = the potential difference between the electrodes, when the electrodes are engaged on the workpiece in the second position.

D = the separation of the electrodes at their points of engagement.

Specific embodiments of the invention will now be described with reference to the following drawings in which.

Figure 1:
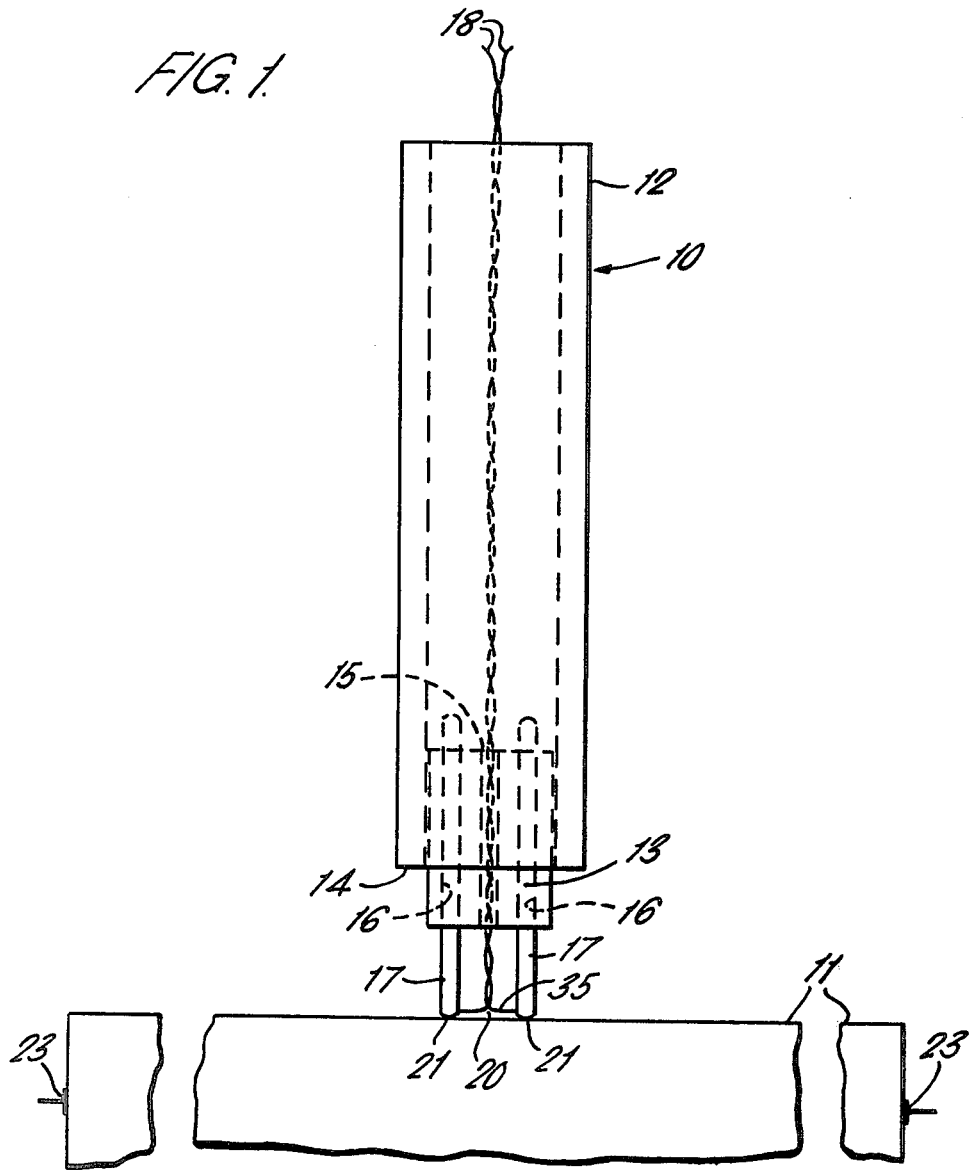
FIG. 1 is an elevation of a workpiece and an electrical probe engaged on the workpiece.

FIG. 1 shows a probe, generally indicated at 10, engaged on the surface of a workpiece 11. The probe comprises an annular aluminium body 12, which has a Bakelite plug 13 engaged in its lower end 14 and projecting therefrom. The plug 13 has a central bore 15 and a pair of further bores 16 extending parallel to the bore 15 and on either side thereof.

A respective elongate metal electrode 17 is engaged in each further bore 16 and projects from the plug 13 downwardly away from the lower end 14 of body 12.

Each electrode 17 has a lead 18. The leads 18 extend as a twisted pair from respective output ends 19, see FIG. 2, through the body 12 and central bore 15, between electrodes 18 to a point 20 which is adjacent the plane containing the free ends 21 of electrodes 17. The free ends 21 constitute the contact surfaces of electrodes 17.

Leads 18 separate at the point 20 and extend directly to their respective electrodes 17 so that their output ends 22 connect with their respective electrodes adjacent their respective free ends or contact surfaces 21.

For the purposes of this specification a "twisted pair" of wires covers a pair of wires which have been mutually twisted such that the respective e.m.f. induced in the twisted sections of the wires when they are placed in a varying magnetic or electric field are substantially equal and opposite and therefore effectively cancel out.

The probe 10 can be used for detecting surface cracks in the workpiece 11 and for measuring their depth. The measurements are carried out by measuring the potential difference between the contact surfaces 21 of the electrodes 17 when an alternating current is passed through the workpiece 11 by means of electrodes 23. The circuit of FIG. 2, which will be described in more detail below, can be utilised for such measurements.

The measurements depend on the existence of an effect known as the skin effect. In this effect it is well known that if one passes an alternating current through a metal, most of the current is carried within a peripheral portion of the conductor which extends to a depth $\delta$ from the surface of the conductor, $\delta$ approximately defined by the following equation:

$$\delta = \sqrt{\frac{1}{\mu\mu_o\sigma\pi f}}$$

where
 $\delta$ = skin depth
 $\mu$ = relative permeability of metal
 $\mu_o$ = permeability of free space
 $\sigma$ = conductivity of metal
 f = frequency of A.C. source By choosing a suitable frequency for the alternating current for any given test material it is possible to cause most of the current to be carried in the outer skin of the metal. The impedance to alternating current between any two points on the surface will depend on the path length between the points and the skin depth. If for a given metal, the frequency is maintained constant the skin depth is constant. It will be appreciated that if a surface crack or defect lies between the two points the path length between the points will be altered and therefore the potential difference between the points will be altered.

Figure 2:
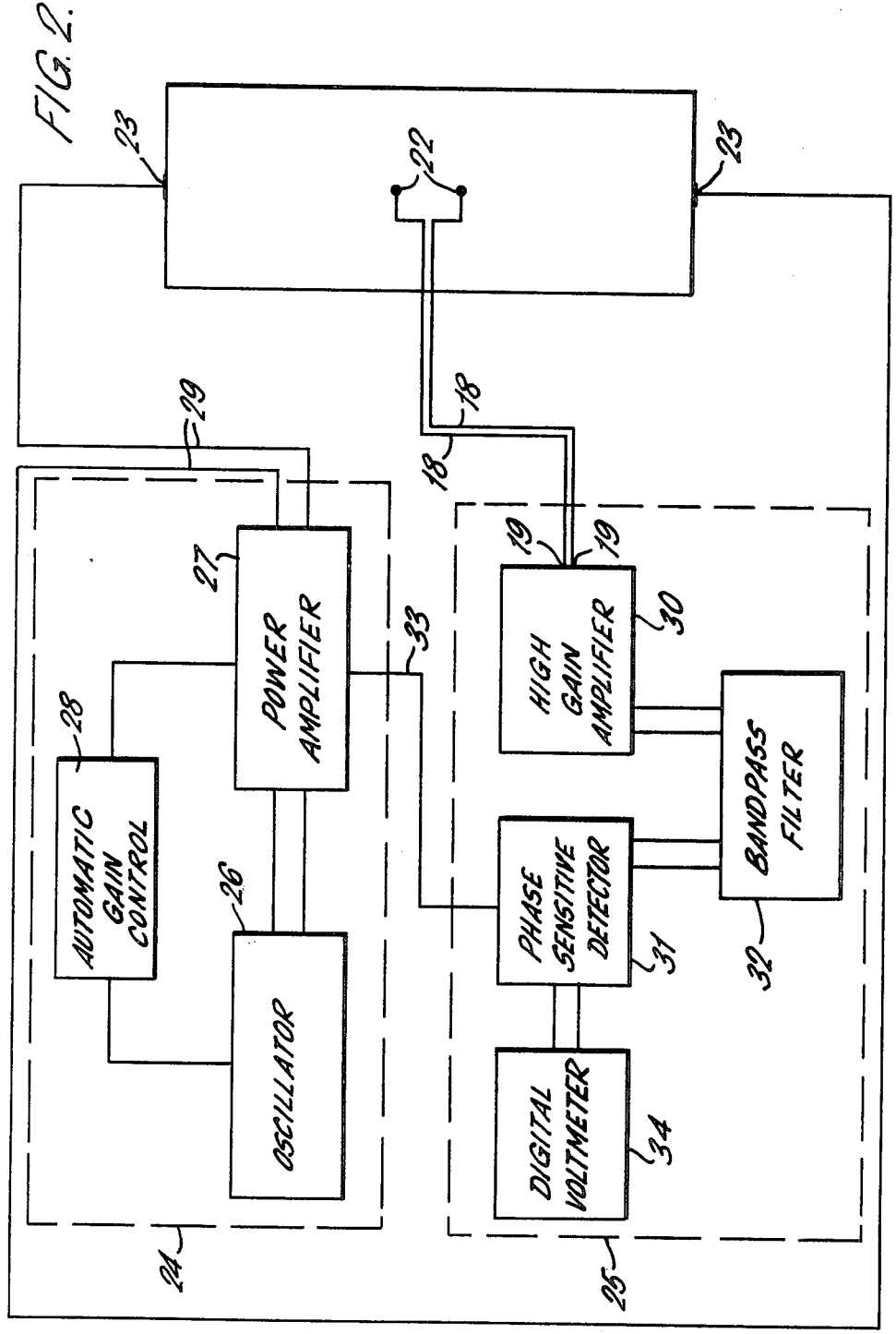
FIG. 2 shows a circuit for use with the probe of FIG. 1.

FIG. 2 shows the circuitry for use with the probe 10. The circuitry comprises an alternating current power source, generally indicated at 24, and the voltage measuring device generally indicated at 25.

The alternating current power source comprises an oscillator 26, and an automatic control circuit 28 to maintain the current flowing in the output leads 29 and workpiece 11 at a substantially constant, although adjustable, value. The frequency of oscillation of the oscillator 26 can be varied so that the frequency of the alternating current can be varied to suit the particular material under test.

The power amplifier 27 has output leads 29, which feed electrodes 23. The output leads 29 should extend away from the electrodes 23 along the line joining the electrodes 23 so that distortion of the field created by the alternating current flowing in the workpiece 11 is reduced to a minimum. Further the current leads 29 should be kept away from leads 18.

The voltage measuring device 25 comprises a high gain amplifier 30, which is preferably constituted by a differential amplifier and which amplifies the potential differenc between contact surfaces 21. The amplified signal is fed to the high gain amplifier by leads 18. The output of the high gain amplifier 30 is fed to phase sensitive detector 31 via a band pass filter 32. The phase sensitive detector 31 can either be linked to the power amplifier 27 by a lead 33 so that it can be used to cancel out of phase pick-up or the phase sensitive detector 31 can be used as a tracking filter and locked to the input signal. The output of the phase sensitive detector 31 is fed to a digital volmeter 34, which displays the measured potential difference between the contact surfaces 21 of electrode 17.

As has been indicated above the probe 10 can be used in two ways. Firstly it can be used to locate cracks. This is done by obtaining a reading for the potential difference which occurs between the contact surfaces 21 when the probe is engaged, in the manner shown in FIG. 1, on a surface of an uncracked portion of the workpiece, or on a calibrating block and a current of particular frequency and magnitude is fed through the workpiece. The probe is then be moved along the surface of the workpiece, which is to be inspected, and the presence of a crack, running between the electrodes 17, will be shown by a reading on the digital voltmeter which is significantly higher than the calibration reading.

It will be appreciated that in order to obtain readings of any accuracy or consistency the probe 10 must be insensitive to the varying magnetic field caused by the current passing through the workpiece and to the probes exact orientation within that magnetic field. For this to be achieved the leads 18 must be arranged to either minimise the inductive pick up in the leads or so as to minimise the effect of induction on the leads. For the purposes of this specification an arrangement of leads which minimises inductive pick up or minimise the effect of induction of the leads is known as "a non-inductive circuit". As the leads 18 are connected as a twisted pair, for that length of the leads, any e.m.f. induced in the leads should cancel out at the high gain amplifier 30. However, the portions 35 of the leads 18 which extend away from point 20 to the electrodes 17 form a conducting loop together with the electrodes 17 and that part of the surface of the workpiece 11 which extends between the contact surfaces 21. It will be appreciated that the e.m.f. induced in this conducting loop will be related to the cross section area of the loop. The area of this loop is determined by two dimensions. The first dimension is the separation of the contact surfaces 21. The second dimension is the average height of the portions 35 above the surface of the workpiece 11. The separation of the contact surfaces 21 is generally determined by other factors, such as the optimum size of the calibration signal having regard to the likely magnitude of the additional "crack" signal. However, this dimension is not critical, because an increase in this dimension also causes an increase in the magnitude of the potential difference to be measured and thus to a great extent gives no change in the signal/noise ratio. The other dimension, i.e. the average height of portions 35 above the surface 21 or workpiece 11 is critical and should be kept to a minimum. Thus preferably the portions 35 of leads 18 should extend along or just above the surface of the workpiece 11 during use.

It will be appreciated that the leads 18 may be screened, or they may be replaced by a coaxial cable.

Figure 3:
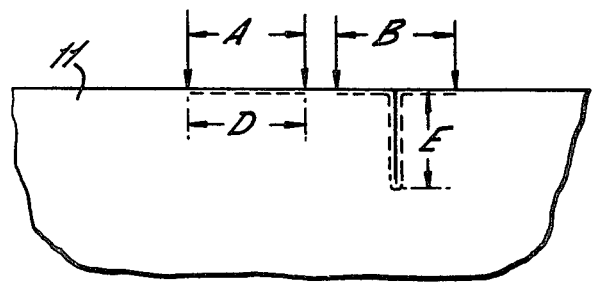
FIG. 3 is a schematic view of the probe positions on a workpiece.

The fact that the probe is designed to be insensitive to the varying magnetic field means that it can be used in the second of the two manners mentioned above. Referring to FIG. 3, after the position of a crack has been located, by any means including visual means, the probe is engaged on the surface of the workpiece 11 immediately adjacent to and one side of the crack. This is the left hand most position in FIG. 3. The potential difference between the contact surfaces 21 is measured and recorded. The probe is then placed so that the crack runs between the electrodes and the potential difference is again recorded.

A crack depth (E) can then be calculated by the following formula:

$$E = (B/A - 1) \times D/2$$

wherein

E = the crack depth.

A = the potential difference between the electrodes when the electrodes are engaged on the workpiece on the first mentioned position.

B = the potential difference between the electrodes, when the electrodes are engaged on the workpiece in the second position.

D = the separation of the electrodes at their points of engagement.

Figure 4:
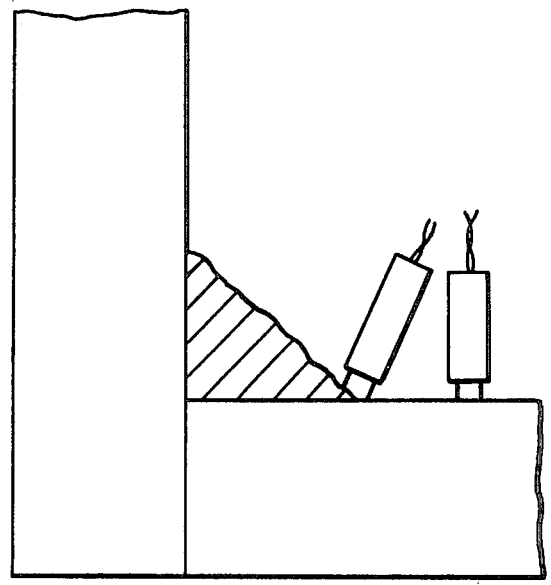
FIG. 4 shows probe positions to be used for cracks in or adjacent to welds.

As the probe 10 is arranged to be insensitive to the fluctuating magnetic field in which it is disposed the probe can be placed in its two positions without worrying greatly about variations in the magnetic field or in the orientation of the probe. As a result of this latter feature the use of the probe need not be limited to flat workpieces but it can be used on a welded workpiece as shown in FIG. 4.

Figure 5:
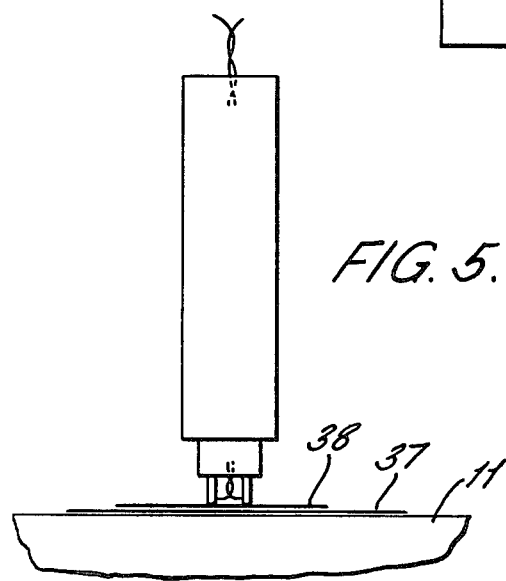
FIG. 5 is an elevation of apparatus for detecting the pickup in a probe.

If for any reason the probe 10 is still not sufficiently insensitive to the varying magnetic field, in any given situation in use, the induced e.m.f. which will occur in any situation can be detected by the following method. Prior to taking the actual measurements a thin layer of insulating material 37 is placed on the surface of workpiece 11 and a thin layer 38 of conductor is placed on top of layer 37. The probe is then engaged on the layer 38, as shown in FIG. 5, and a reading of the potential difference between the contact surfaces 21 is taken. As the contact surfaces 21 are insulated from the workpiece 11 only the induced or pick-up e.m.f. will be measured by the voltage measuring device 25. The voltage measuring device 25 can then be provided with means for removing the measured pick-up e.m.f. from any further readings taken on that workpiece.

Figure 6:
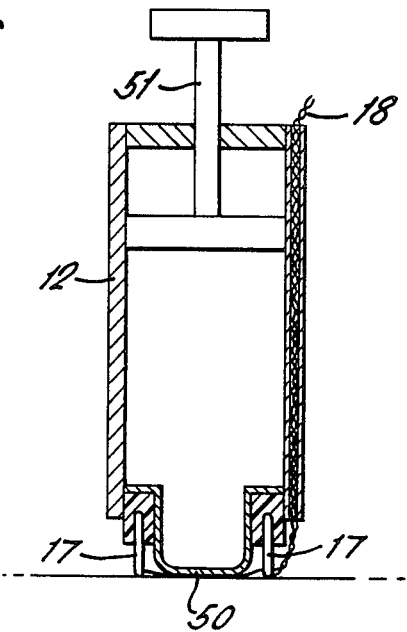
FIG. 6 is a cross sectional view of second form of electrical probe.
Figure 7:
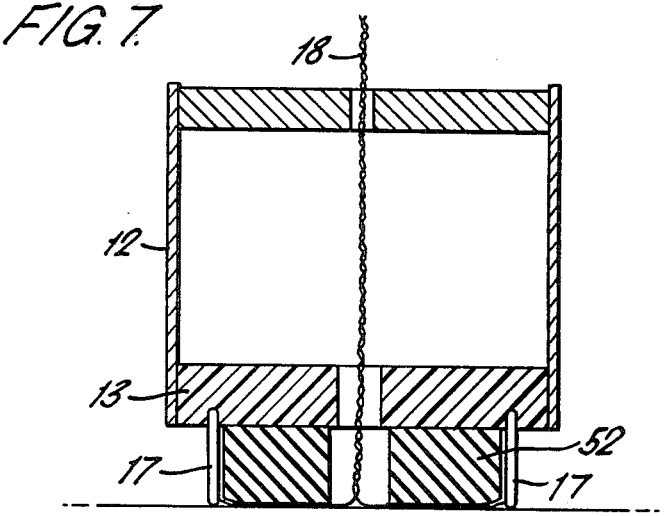
FIG. 7 is a cross sectional view of a third form of electrical probe.

In an alternative form of the probe 10 the portions 35 may be mounted or formed on a flexible diaphragm 50 see FIG. 6, which is supported on a tube, (not shown) mounted on the body 12. In use gas can be blown into the hollow portion of the body 12 through apertures in plug 13 to deflect the diaphragm against the surface of the workpiece 11. Alternatively the diaphragm 50 may be biased against the surface of the workpiece by depression of a plunger 51 arranged for axial movement in the body 12 or by a spring acting between the body 12 or plug 13 of the diaphragm. In a still further alternative, means may be provided for directly urging the leads against the surface of the workpiece. For example, the bias means may be constituted by a rubber block held under compression (see FIG. 7). It will be appreciated that this arrangement will quickly reduce the magnitude of the e.m.f. induced in the leads 18, because it reduces the area of the loop described above almost to zero. This arrangement is particularly useful when the probe is being used on surfaces which are curved.

It will be appreciated that in any of the above embodiments the twisted pair of leads 18 may be replaced by any non-inductive pair such as a coaxial cable.

If a probe is to be used to detect cracks in a weld toe on a weld between two right angular members, the probe 10 can be advantageously be provided with a spring trailing arm on either side to maintain the position of the electrodes relative to the toe as the probe is drawn along the toe.

The probe 10 may be used to monitor changes in crack depth by engaging the probe 10 on the workpiece 11 across a crack and monitoring the potential difference between the electrodes. A reference probe may be used. If so, the reference probe is engaged adjacent and to one side of the the crack and the potential difference across the electrodes compared with the potential difference across the electrodes of the monitoring probe.

We claim:

1. An electrical probe for apparatus for measuring crack depths in workpieces, comprising a body, a pair of electrodes mounted on the body at spaced locations thereon each electrode having a contact surface for engaging a work piece, the electrodes being electrically insulated from one another, electric lead means for the respective electrodes, each lead means having an input end and an output end, and means for connecting the input ends of the lead means to the respective electrodes, the lead means and electrodes together constituting a non-inductive circuit and means to connect the output ends of said lead means to a source of alternating current.

2. An electrical probe for apparatus for measuring crack depths in workpieces, comprising a body, a pair of electrodes mounted on the body at spaced locations thereon, each electrode having a contact surface for engaging a workpiece, the electrodes being electrically insulated one from the other, electric lead means for the respective electrodes, and means to connect the lead means to the electrodes to form, with a workpiece engaged by the electrode contact surfaces, a loop the area of which is negligible and means to connect said lead means to a source of alternating current.

3. An electrical probe for apparatus for measuring crack depths in workpieces, comprising a body, a pair of electrodes mounted on the body at spaced locations thereon, each electrode having a contact surface for engaging a workpiece, the electrodes being electrically insulated one from the other, electric lead means for the respective electrodes, each lead means having an input end and an output end, the two lead means extending from the respective output ends as a coaxial cable to a position in or immediately adjacent a plane containing said contact surfaces of the electrodes, the leads separating at said position and extending directly to their respective electrodes, and means to connect the input ends of the lead means to the respective electrodes adjacent the contact surfaces thereof and means to connect the output ends of said lead means to a source of alternating current.

4. An electrical probe for apparatus for measuring crack depths in workpieces, comprising a body, a pair of electrodes mounted on the body at spaced locations thereon, each electrode having a contact surface for engaging a workpiece the electrodes being electrically insulated one from the other, electric lead means for the respective electrodes, each lead means having an input end and an output end, the two lead means extending from the respective output ends as a twisted pair to a position in or immediately adjacent a plane containing said contact surfaces of the electrodes, the leads separating at said position and extending directly to their respective electrodes, and means to connect the input ends of the lead means to the respective electrodes adjacent the contact surfaces thereof and means to connect the output ends of said lead means to a source of alternating current.

5. An electrical probe as claimed in claim 4, wherein the twisted pair is shielded.

6. An electrical probe as claimed in any one of claims 1 to 5, wherein each electrode is constituted by an elongate member projecting longitudinally from the body and wherein each contact surface is formed at the free end of its respective electrode.

7. An electrical probe as claimed in claim 6, wherein the electrodes extend parallel with each other.

8. An electrical probe as claimed in any one of claims 3 and 4, wherein means are provided for urging those portions of the lead means which extend directly to the respective electrodes against the surface of a workpiece when, in use, the electrodes are positioned to engage the surface of the workpiece.

9. An electric probe as claimed in claim 8, wherein said portions of the lead means are mounted or formed on one side of a flexible diaphragm and the means for urging comprises means for exerting a pressure on the other side of the diaphragm.

10. An electrical probe as claimed in claim 9 wherein the means for exerting pressure includes a source of pressurized gas.

11. An electrical probe as claim in claim 9 wherein the means for urging comprises at least one rubber block mounted on the body to project between the electrodes and engage the said portions of the lead means.

12. Apparatus for measuring the depth of surface cracks in an electrically conducting workpiece comprising a pair of current input leads engageable on the workpiece on respective sides of the crack, means for passing an alternating current through the leads and through the workpiece, a probe as claimed in any one of claims 1 to 4 and means for detecting the potential difference between the electrodes of the probe.

13. Apparatus as claimed in claim 12 wherein the means for detecting the potential difference between the electrodes includes a phase sensitive detector.

14. A method of measuring the depth of a surface crack in the electrically conducting workpiece comprising the steps of passing an alternating current through that part of the workpiece which contains the crack, engaging a pair of spaced electrodes on the surface of the workpiece adjacent to and on one side of the crack, measuring the potential difference between the electrodes, engaging the electrodes on the surface such that the crack runs between the electrodes whilst maintaining the separation of the electrodes, measuring the potential difference between the electrodes and calculating the crack depth in accordance with the formula:

$$E = (B/A - 1) \times D/2$$

wherein
E = the crack depth;
A = the potential difference between the electrodes when the electrodes are engaged in the workpiece on the first mentioned position;
B = the potential difference between the electrodes when the electrodes are engaged on the workpiece in the second position;
D = the separation of the electrodes at their points of engagement.

15. A method as claimed in claim 14 comprising performing, the steps of placing a thin sheet of insulating material over the surface in respect of which measurement A is taken, covering the sheet of insulating material with a thin sheet of conducting material, engaging the electrodes on the sheet of conducting material, passing current through the workpiece measuring the potential difference between the electrodes and deducting the measured potential difference from A and B before calculating E.

16. A method of monitoring changes in crack depth in a workpiece comprising the steps of passing an alternating current through that part of the workpiece which contains the crack, engaging the electrodes of a probe as claimed in anyone of claims 1 to 4 on the workpiece to bridge the gap, measuring the potential difference between the electrodes and monitoring changes in the potential difference.

17. A method as claimed in claim 16 further comprising the steps of placing a further such probe 1 to 4 onto the workpiece adjacent to and to one side of the crack, measuring the potential difference between the electrodes of the further probe and comparing the potential differences measured across the two probes.

* * * * *

UNITED STATES PATENT AND TRADEMARK OFFICE
CERTIFICATE OF CORRECTION

PATENT NO. : 4,266,185

DATED : May 5, 1981

INVENTOR(S) : Frank David Watts Charlesworth et al.

It is certified that error appears in the above—identified patent and that said Letters Patent is hereby corrected as shown below:

Column 8, line 52, after "probe" delete "1 to 4".

Signed and Sealed this

Fourth Day of August 1981

[SEAL]

Attest:

GERALD J. MOSSINGHOFF

Attesting Officer     Commissioner of Patents and Trademarks